United States Patent [19]

Sonobe et al.

[11] 4,051,179
[45] Sept. 27, 1977

[54] CATALYTIC PROCESS FOR THE PREPARATION OF UNSATURATED CARBOXYLIC ACIDS

[75] Inventors: Hiroshi Sonobe, Otake; Masaaki Kato, Yamaguchi; Hideo Matsuzawa, Otake; Hiromichi Ishii, Otake; Masao Kobayashi, Otake, all of Japan

[73] Assignee: Mitsubishi Rayon Co., Ltd., Tokyo, Japan

[21] Appl. No.: 667,677

[22] Filed: Mar. 17, 1976

[30] Foreign Application Priority Data

Apr. 3, 1975 Japan .................................. 50-40660

[51] Int. Cl.² .............................................. C07C 51/32
[52] U.S. Cl. .............................. 260/530 N; 252/435; 252/437
[58] Field of Search .................... 260/530 N; 252/435, 252/437

[56] References Cited

U.S. PATENT DOCUMENTS

| 3,773,692 | 11/1973 | Hensel | 260/530 N |
| 3,795,703 | 3/1974 | Nünn et al. | 60/530 N |
| 3,875,220 | 4/1975 | White et al. | 260/530 N |

Primary Examiner—Vivian Garner

Attorney, Agent, or Firm—Oblon, Fisher, Spivak, McClelland & Maier

[57] ABSTRACT

The gas phase catalytic oxidation of an unsaturated aldehyde with molecular oxygen at 240° to 390° C to give the corresponding unsaturated carboxylic acid is conducted in the presence of a catalyst represented by the following formula:

$$P_a Mo_b As_c X_d Y_e Z_f O_g$$

wherein $a$, $b$, $c$, $d$, $e$, $f$ and $g$ represent the atomic ratio of each component and $a$ is 0.03 to 0.2, $b$ is 1, $c$ is 0.015 to 0.15, $d$ is 0.003 to 1, $e$ is 0.003 to 0.417, $f$ is 0.003 to 1, and $g$ is a value determined by the valencies of the elements present in the catalyst; and wherein X is copper, vanadium or mixtures thereof Y is at least one alkali metal selected from the group consisting of lithium, sodium, potassium, rubidium and cesium, and Z is at least one metal selected from the group consisting of magnesium, aluminum, calcium, titanium, zirconium, silver, antimony, tellurium, barium, tantalum and silicon. This catalyst is especially effective for the preparation of methacrylic acid from methacrolein, and has a very long lifetime.

10 Claims, No Drawings

CATALYTIC PROCESS FOR THE PREPARATION OF UNSATURATED CARBOXYLIC ACIDS

BACKGROUND OF THE INVENTION

1. Field of the Invention

This invention relates to a process for preparing unsaturated carboxylic acids from unsaturated aldehydes in the presence of a phosphorus - molybdenum - arsenic - alkali metal type catalyst which contains two or more other metals.

2. Description of the Prior Art

Various catalysts have been known for use in the gas phase catalytic oxidation of unsaturated aldehydes such as those disclosed in U.S. Pat. Nos. 3,475,488; 3,567,773; 3,646,127; 3,649,684; 3,686,294 and 3,761,516 and DT 2,251,364. Included among these catalysts are molybdenum - vanadium catalysts which exhibit excellent results in the oxidation of acrolein. However, these catalysts are not suitable for the oxidation of methacrolein. Phosphorus - molybdenum - arsenic catalysts of specific compositions are known to give good results in the oxidation of methacrolein. However, these catalysts are still insufficient because several problems still remain to be solved. For instance these catalysts have a very short lifetime. Other types of catalysts do not give good results in the oxidation of methacrolein. A need, therefore, continues to exist for a catalyst for the oxidation of unsaturated aldehydes such as acrolein and methacrolein to the corresponding unsaturated acids which exhibits excellent catalytic effects and which has a good lifetime.

SUMMARY OF THE INVENTION

Accordingly, one object of this invention is to provide a process for preparing unsaturated carboxylic acids, especially methacrylic acid, in high yield from unsaturated aldehydes especially methacrolein.

Another object of this invention is to provide a catalyst having a long lifetime which enables production of unsaturated carboxylic acids in high yield when used for the catalytic oxidation of unsaturated aldehydes.

Briefly, these objects and other objects of the invention as hereinafter will become more readily apparent have been attained by a process for the preparation of unsaturated carboxylic acids, which comprises catalytically oxidizing an unsaturated aldehyde in the gas phase at a temperature of 240° to 390° C with molecular oxygen to form the corresponding unsaturated carboxylic acid, wherein the catalytic oxidation is performed in the presence of a catalyst of the following formula:

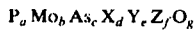

$$P_a Mo_b As_c X_d Y_e Z_f O_g$$

wherein $a$, $b$, $c$, $d$, $e$, $f$ and $g$ represent the atomic ratio of each component and $a$ is 0.03 to 0.2, $b$ is 1, $c$ is 0.015 to 0.15, $d$ is 0.003 to 1, $e$ is 0.003 to 0.417, $f$ is 0.003 to 1, and $g$ is a value determined by the valencies of the elements present in the catalyst, and wherein X is copper and/or vanadium, Y is at least one alkali metal selected from the group consisting of lithium, sodium, potassium, rubidium and cesium, and Z is at least one metal selected from the group consisting of magnesium, aluminum, calcium, titanium, zirconium, silver, antimony, tellurium, barium, tantalum and silicon.

DESCRIPTION OF THE PREFERRED EMBODIMENTS

The atomic ratio of each component in the catalyst used in this invention is critical, and if the atomic ratios are outside the specified ranges, catalysts having the desired properties are not obtained. The amount of metal element X must be chosen within the range, expressed in terms of the atomic ratio relative to molybdenum, of from 0.003 to 1. It is preferred that the atomic ratio of the metal X to molybdenum be within the range of from 0.003 to 0.25, especially 0.006 to 0.2. When both of these metals are present, it is preferred that the sum of the atomic ratio of the metals relative to molybdenum be within the above range. If the atomic ratio is below this range, a sufficient catalytic effect is not obtained. If the atomic ratio is above this range, the catalyst lifetime is further prolonged but the selectivity to the desired unsaturated acid product is decreased.

The amount of the alkali metal component Y in the catalyst composition must be within the range, expressed in terms of the atomic ratio relative to molybdenum, of from 0.003 to 0.417, especially from 0.01 to 0.25. If the amount of the alkali metal Y is greater than this range, a reduction in the selectivity to the desired unsaturated acid product is observed.

The amount of metal Z in the composition must be chosen within the range, expressed in terms of the atomic ratio relative to molybdenum, of from 0.003 to 1. It is preferred that the atomic ratio of the metal Z be 0.003 to 0.25. When two or more of these metals are present, it is preferred that the sum of the atomic ratio of the metals relative to molybdenum be within the above range. If the atomic ratio is below this range, a sufficient catalytic effect is not obtained. If the atomic ratio is above this range, the selectivity to the desired unsaturated acid product is decreased. The elements antimony and tantalum are preferred selections for Z.

Since the chemical state of each component element in the catalyst of this invention is very complicated, the chemical state of each element in the catalyst has not been completely elucidated. However, it is believed that each component is not simply present in the form of a mere oxide but rather is in the form of a heteropolyacid compound. In the catalyst of this invention, an ammonium group introduced from the starting materials used for the catalyst may be present. Therefore, some portions of the heteropoly - acid in the catalyst may be combined as a salt with the ammonium group.

When the elements represented by X and Z are incorporated in a catalyst composed of molybdenum, phosphorus, arsenic, alkali metal(s) and oxygen, the catalyst lifetime is substantially improved. The reason has not been completely elucidated. But in view of the known fact that in a molybdenum - containing catalyst, when the concentration of adsorbed oxygen is lowered, the activity and selectivity are reduced, it is theorized that the concentration of adsorbed oxygen is increased by the presence of the elements X and Z and hence, the activity is elevated and the catalyst lifetime is prolonged.

The catalyst of this invention is heat-treated at a temperature of 300° to 500° C before it is used in the oxidation reaction. A preferred heat treatment is within the range of from 380° to 450° C. If the heat treatment temperature exceeds 500° C, both the activity and selectivity of the catalyst are reduced. The lower heat treatment temperature limit is not as critical. However, at a heat treatment temperature not exceeding about 300° C, it is difficult to obtain a catalyst having stable properties. The heat treatment time varies depending on the heat treatment temperature, but in general, it is preferred that the heat treatment be conducted for from 30 minutes to several days. It is also desired that the heat treatment be conducted in air or in air diluted with an inert gas. If necessary, a heat treatment atmosphere of air containing a reducing substance at low concentrations can be used.

The preparation of the catalyst to be used in this invention can be accomplished using methods known to those skilled in the art. It is desired that the starting materials be intimately mixed with one another, but the method of mixing is not particularly critical. Irregular distribution of the components of the composition can be avoided by any of the conventional methods such as evaporation-to-dryness, precipitation, oxide-mixing or the like.

Suitable starting materials for the catalyst preparation include ammonium compounds such as ammonium molybdate, ammonium phosphate, ammonium phosphomolybdate, ammonium arsenomolybdate, or the like. Elements represented by X can be used as the oxides, nitrates, ammonium salts or the like, and the alkali elements represented by Y can be used as the oxides, nitrates, hydroxides or the like. The catalyst can be obtained by drying a homogeneous mixture of the starting materials and then heat treating the mixture at a temperature of from 300° to 500° C for from 30 minutes to several days.

The type of reaction vessel in which the catalyst of the invention is packed is not particularly critical, and either a fixed bed or a fluidized bed reactor can be used in this invention. Suitable unsaturated aldehydes which can be oxidized in the process of this invention include acrolein, methacrolein, and mixtures of acrolein and methacrolein. The process of this invention is especially effective for the oxidation of methacrolein. Methacrolein which is obtained by the catalytic oxidation of isobutylene or tertiary butanol can be used as is or after it has been purified.

The concentration of the unsaturated aldehyde in the feed gas can be varied within a broad range, but it is generally preferred that the concentration of the unsaturated aldehyde be within the range of from 1 to 20% by volume, especially 3 to 15% by volume. Molecular oxygen is used as the oxidant in the process of this invention. Preferably, air is used from the economic viewpoint. If necessary, an oxidant of air enriched with pure oxygen can also be used. It is also preferred that the concentration of oxygen in the feed gas, expressed in terms of its mole ratio relative to the unsaturated aldehyde, be within the range of 0.3 to 4, especially 0.4 to 2.5. The starting gaseous mixture may be diluted with an inert gas such as nitrogen, steam, carbon dioxide or the like. The oxidation reaction is conducted under a pressure ranging from atmospheric pressure to several atmospheres. The space velocity of the feed gas varies depending on the reaction temperature and pressure, but it is generally preferred that the starting gaseous mixture be fed at a space velocity of from 300 hr$^{-1}$ to 10,000 hr$^{-1}$. The reaction temperature can be chosen within the range of from 240° to 390° C, but it is generally preferred that the reduction temperature range from 270° to 340° C. One of the characteristic features of this invention is that the oxidation reaction can be performed at such relatively low temperatures.

Having generally described this invention, a further understanding can be obtained by reference to certain specific examples which are provided herein for purposes of illustration only and are not intended to be limiting unless otherwise specified. In the Examples, the term "parts" is by weight and the selectivity to the unsaturated carboxylic acid is expressed in terms of the ratio (percent) of the molar amount of the unsaturated carboxylic acid product to the molar amount of the reacted unsaturated aldehyde. The yield of the unsaturated carboxylic acid is expressed in terms of the ratio of the molar amount of the unsaturated carboxylic acid product to the molar amount of the charged unsaturated aldehyde. The reaction time was measured from the point at which the reaction conditions described in the Examples were actually established.

EXAMPLE 1

177 Parts of ammonium paramolybdate were dissolved in 500 parts of pure water maintained at about 60° C, and 9.6 parts of 85% phosphoric acid and 14.2 parts of a 50% aqueous solution of arsenic acid were added to the solution. Then, a solution of 40.4 parts of copper nitrate in 100 parts of water and a solution of 4.88 parts of ammonium metavanadate in 150 parts of water were added to the mixture. Thereafter, a solution of 8.44 parts of potassium nitrate and 10.75 parts of magnesium nitrate in 100 parts of water was further added to the mixture. The resulting mixed solution was evaporated to dryness by heating with agitation, and the resulting solid was dried at 130° C for 16 hours. The resulting dried solid was pulverized in a ball mill, compression-molded, placed in an electric furnance and heat treated. The heat treatment was performed by elevating the temperature from 100° C to 400° C at a rate of 20° C per hour, and then maintaining the solid at 400° C for 5 hours. The catalyst so obtained contained the phosphorus and metal components in the following atomic ratio:

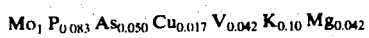

$Mo_1 P_{0.083} As_{0.050} Cu_{0.017} V_{0.042} K_{0.10} Mg_{0.042}$

This catalyst was packed in a fixed bed reaction vessel and maintained at 290° C. A gaseous mixture comprising 5% by volume methacrolein, 10% by volume oxygen, 20% by volume steam and 65% by volume nitrogen was fed into the reaction vessel at a space velocity of 1000 hr$^{-1}$. Under these conditions, the reaction was conducted for 2000 hours. The reactiongas discharged from the reaction vessel was analyzed by gas chromatography or the like to determine the activity of the catalyst. Results are shown in Table 1.

Table 1

| Reaction Time (hours) | Conversion of Methacrolein (%) | Selectivity to Methacrylic acid (%) | Yield of Methacrylic acid (%) |
|---|---|---|---|
| 4 | 95.0 | 95.0 | 90.3 |
| 2000 | 94.8 | 95.0 | 90.1 |

EXAMPLE 2

The oxidation of acrolein was conducted with the use of the catalyst prepared in Example 1. The starting gaseous mixture comprised 5% by volume acrolein, 10% by volume oxygen, 20% by volume steam and 65% by volume nitrogen. The reaction temperature was adjusted to 300° C. The other operational procedures and conditions were the same as those described in Example 1. The yield of acrylic acid was 90.1% and after the lapse of 2000 hours, the results obtained using the same catalyst were substantially the same as those shown.

EXAMPLES 3-14

Catalysts were prepared in the same manner as described in Example 1 except for variations in the compositions and atomic ratios. The catalysts so obtained are shown in Table II.

Using these catalysts, oxidations of methacrolein were conducted under the same conditions as described in Example 1 except for the reaction temperatures. The results of the experiments are summarized in Table II.

Table II

| Ex. No. | Catalyst composition and Atomic Ratio | Reaction Temp. | Yield of Methacrylic Acid |
|---|---|---|---|
| 3 | $P_{0.083}Mo_1As_{0.05}Cu_{0.017}V_{0.042}$ | 300° C | 92.0% |
| 4 | $Na_{0.017}K_{0.083}Al_{0.083}$<br>$P_{0.083}Mo_1As_{0.05}Cu_{0.017}V_{0.042}$ | 290° C | 90.5% |
| 5 | $Li_{0.017}Cs_{0.083}Si_{0.333}$<br>$P_{0.083}Mo_1As_{0.05}Cu_{0.017}V_{0.042}$ | 300° C | 90.3% |
| 6 | $K_{0.083}Rb_{0.042}Ca_{0.042}Ti_{0.083}$<br>$P_{0.083}Mo_1As_{0.05}Cu_{0.017}V_{0.042}$ | 290° C | 91.5% |
| 7 | $K_{0.083}Zr_{0.083}$<br>$P_{0.083}Mo_1As_{0.05}Cu_{0.017}V_{0.042}$ | 295° C | 92.0% |
| 8 | $K_{0.125}Si_{0.083}Ag_{0.017}$<br>$P_{0.083}Mo_1As_{0.0325}Cu_{0.021}$ | 300° C | 91.0% |
| 9 | $K_{0.083}Te_{0.042}$<br>$P_{0.083}Mo_1As_{0.0325}Cu_{0.021}$ | 300° C | 90.5% |
| 10 | $V_{0.042}K_{0.083}Si_{0.083}Ba_{0.042}$<br>$P_{0.083}Mo_1As_{0.0325}Cu_{0.021}$ | 300° C | 92.0% |
| 11 | $K_{0.083}Ta_{0.125}$<br>$P_{0.083}Mo_1As_{0.05}Cu_{0.017}K_{0.083}$ | 300° C | 91.0% |
| 12 | $Sb_{0.083}$<br>$P_{0.083}Mo_1As_{0.05}V_{0.042}K_{0.083}$ | 300° C | 92.0% |
| 13 | $Ta_{0.125}$<br>$P_{0.083}Mo_1As_{0.05}V_{0.042}K_{0.083}$ | 300° C | 91.4% |
| 14 | $Te_{0.042}$<br>$P_{0.083}Mo_1As_{0.05}V_{0.042}K_{0.083}$<br>$Sb_{0.083}$ | 300° C | 92.0% |

Having now fully described the invention, it will be apparent to one of ordinary skill in the art that many changes and modifications can be made thereto without departing from the spirit or scope of the invention as set forth herein.

WHAT IS CLAIMED AS NEW AND INTENDED TO BE COVERED BY LETTERS PATENT IS:

1. A process for the preparation of unsaturated carboxylic acids, which comprises catalytically oxidizing acrolein, methacrolein or mixtures thereof in the gas phase at a temperature of 240° to 390° C with molecular oxygen to form the corresponding unsaturated carboxylic acid in the presence of a catalyst having the composition

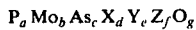

$$P_a Mo_b As_c X_d Y_e Z_f O_g$$

wherein $a$, $b$, $c$, $d$, $e$, $f$ and $g$ represent the atomic ratios of each component and $a$ is within the range of 0.03 to 0.2, $b$ is 1, $c$ is within the range of 0.015 to 0.15, $d$ is within the range of 0.003 to 1, $e$ is within the range of 0.003 to 0.417, $f$ is within the range of 0.003 to 1, and $g$ is a value determined by the degree of oxidation of the elements present in the catalyst, and wherein X is copper, vanadium, or a mixture thereof, Y is at least one alkali metal selected from the group consisting of lithium, sodium, potassium rubidium and cesium, and Z is at least one metal selected from the group consisting of magnesium, aluminum, calcium, titanium, zirconium, silver, antimony, tellurium, barium, tantalum and silicon.

2. The process of claim 1, wherein the unsaturated aldehyde is methacrolein.

3. The process of claim 1, wherein the metal X is copper.

4. The process of claim 1, wherein metals X are a mixture of copper and vanadium.

5. The process of claim 1, wherein the metal Z is antimony.

6. The process of claim 1, wherein the metal Z is tantalum.

7. The process of claim 1, wherein $d$ is 0.003 to 0.25.

8. The process of claim 1, wherein $d$ is 0.006 to 0.2.

9. The process of claim 1, wherein $e$ is 0.01 to 0.25.

10. The process of claim 1, wherein $f$ is 0.003 to 0.25.

* * * * *